US008012323B2

(12) United States Patent
Singh et al.

(10) Patent No.: US 8,012,323 B2
(45) Date of Patent: Sep. 6, 2011

(54) COMPACT ELECTROCHEMICAL BIFUNCTIONAL $NO_x/O_2$ SENSORS WITH INTERNAL REFERENCE FOR HIGH TEMPERATURE APPLICATIONS

(75) Inventors: Dileep Singh, Naperville, IL (US); Jules Routbort, Hinsdale, IL (US); Prabir Dutta, Worthington, OH (US); John V. Spirig, North Brunswick, NJ (US); Jiun Chan Yang, Skokie, IL (US)

(73) Assignee: UChicago Argonne, LLC, Chicago, IL (US)

( * ) Notice: Subject to any disclaimer, the term of this patent is extended or adjusted under 35 U.S.C. 154(b) by 386 days.

(21) Appl. No.: 12/402,216

(22) Filed: Mar. 11, 2009

(65) Prior Publication Data

US 2009/0288961 A1 Nov. 26, 2009

Related U.S. Application Data

(60) Provisional application No. 61/035,962, filed on Mar. 12, 2008.

(51) Int. Cl.
G01N 27/26 (2006.01)
G01N 27/27 (2006.01)
G01N 27/407 (2006.01)
G01N 27/409 (2006.01)
G01N 27/417 (2006.01)
G01N 27/419 (2006.01)

(52) U.S. Cl. ........ 204/424; 204/425; 204/426; 204/427; 205/781; 205/782; 205/784; 205/784.5; 205/785.5

(58) Field of Classification Search .................. 204/424, 204/425, 426, 427; 205/781, 782, 784, 784.5, 205/785.5
See application file for complete search history.

(56) References Cited

U.S. PATENT DOCUMENTS

| | | | |
|---|---|---|---|
| 3,915,830 A | 10/1975 | Isenberg | |
| 4,284,486 A | 8/1981 | Shinohara et al. | |
| 4,502,939 A | 3/1985 | Holfelder et al. | |
| 4,808,293 A | 2/1989 | Fukuda et al. | |
| 4,810,350 A * | 3/1989 | Mantese et al. | 204/412 |
| 5,217,588 A * | 6/1993 | Wang et al. | 205/781 |
| 5,304,294 A * | 4/1994 | Wang et al. | 204/426 |
| 5,360,528 A | 11/1994 | Oh et al. | |
| 5,543,025 A | 8/1996 | Garzon et al. | |
| 5,695,624 A | 12/1997 | Garzon et al. | |
| 5,827,415 A | 10/1998 | Gür et al. | |
| 6,440,028 B2 | 8/2002 | Kim et al. | |
| 6,843,900 B2 * | 1/2005 | Dutta et al. | 204/424 |
| 7,611,613 B2 * | 11/2009 | Dutta et al. | 204/426 |
| 2003/0029910 A1 | 2/2003 | Goretta et al. | |
| 2003/0121780 A1 * | 7/2003 | Dutta et al. | 204/424 |
| 2007/0029210 A1 * | 2/2007 | Dutta et al. | 205/781 |
| 2009/0026076 A1 * | 1/2009 | Yang | 204/412 |
| 2009/0078025 A1 * | 3/2009 | Singh et al. | 73/31.04 |

* cited by examiner

*Primary Examiner* — Bruce Bell
(74) *Attorney, Agent, or Firm* — Foley & Lardner LLP

(57) ABSTRACT

A bifunctional total $NO_x$ and $O_2$ sensor assembly with an internal reference for high temperature sensing. Two electrochemical total $NO_x(NO+NO_2)$ measuring systems and method were coupled with a metal/metal oxide internal oxygen reference to detect $O_2$ and $NO_x$ simultaneously in a combustion environment using a single sensor. A Pd/PdO-containing reference chamber was sealed within a stabilized zirconia superstructure by a high pressure/temperature bonding method. An amperometric and potentiometric $NO_x$ sensor assembly was built on the outside of the Pd/PdO chamber. Pt-loaded zeolite Y was used to obtain total $NO_x$ capacity and also to cover the Pt electrodes for detecting oxygen in the presence of $NO_x$.

20 Claims, 8 Drawing Sheets

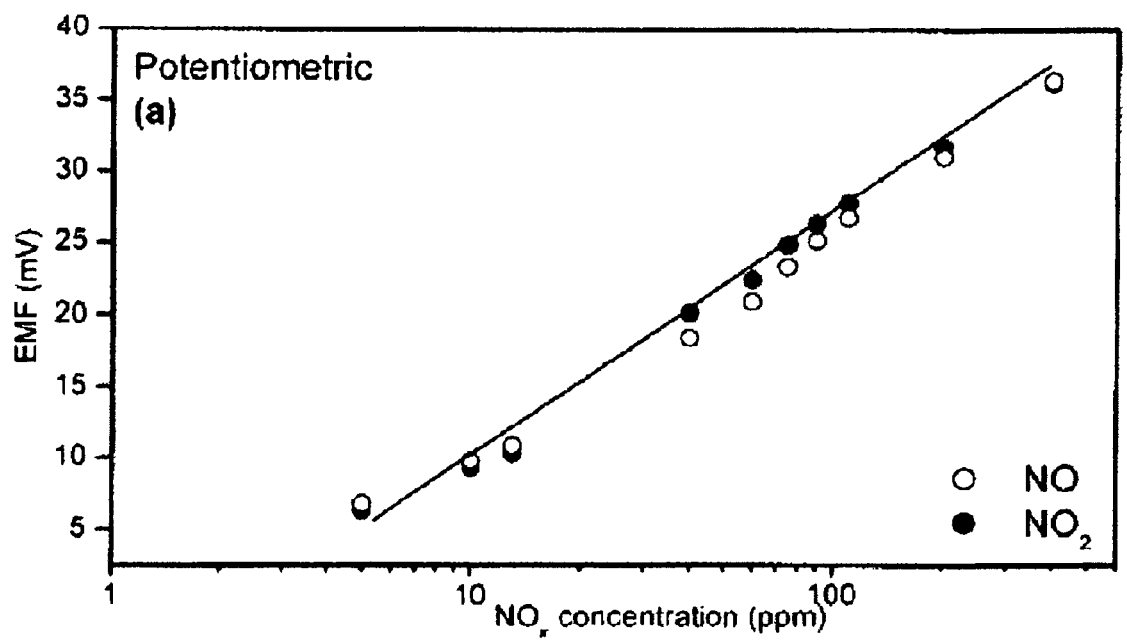
Figure 5(a)
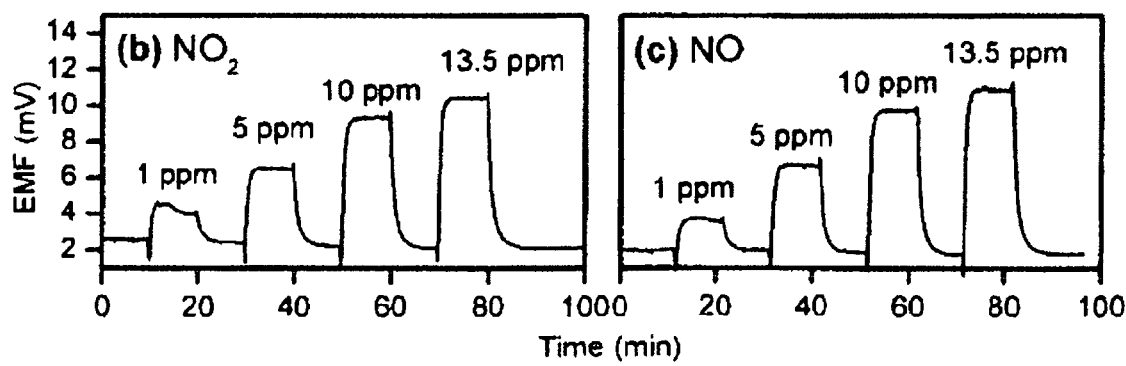
Figure 5(b)  Figure 5(c)

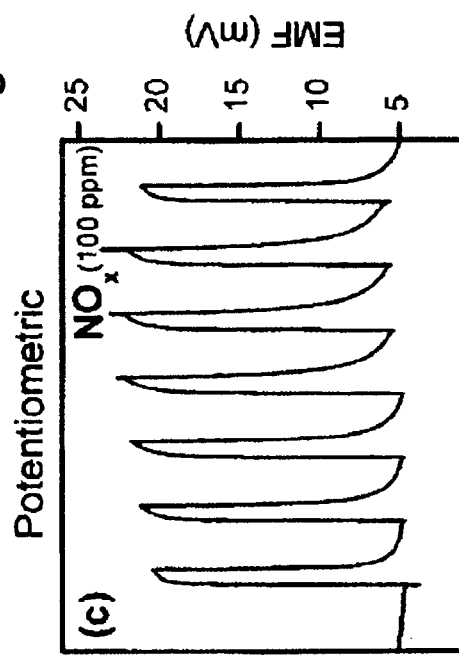
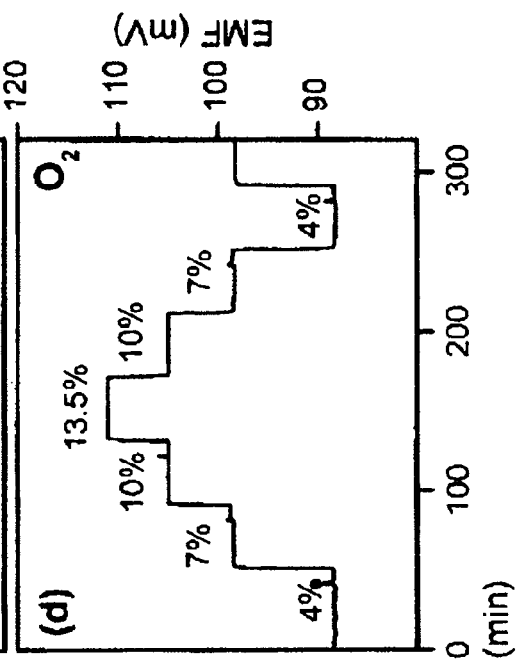
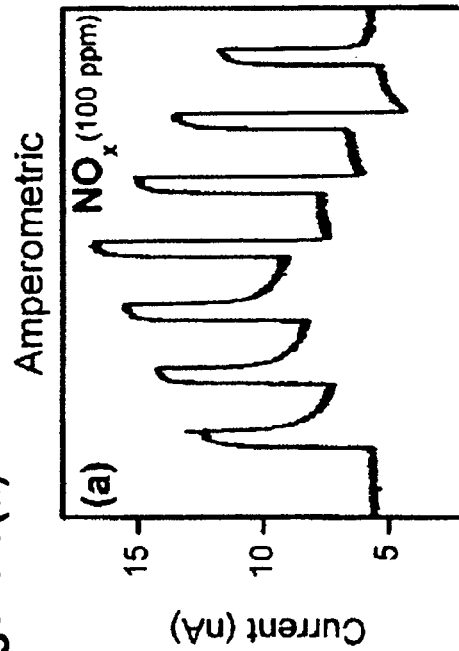
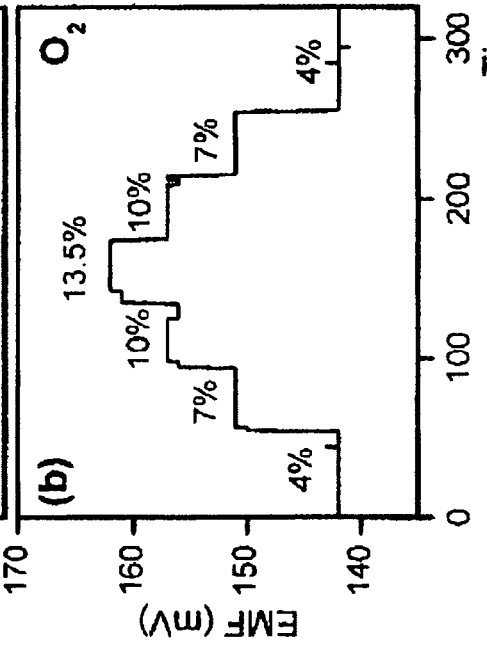

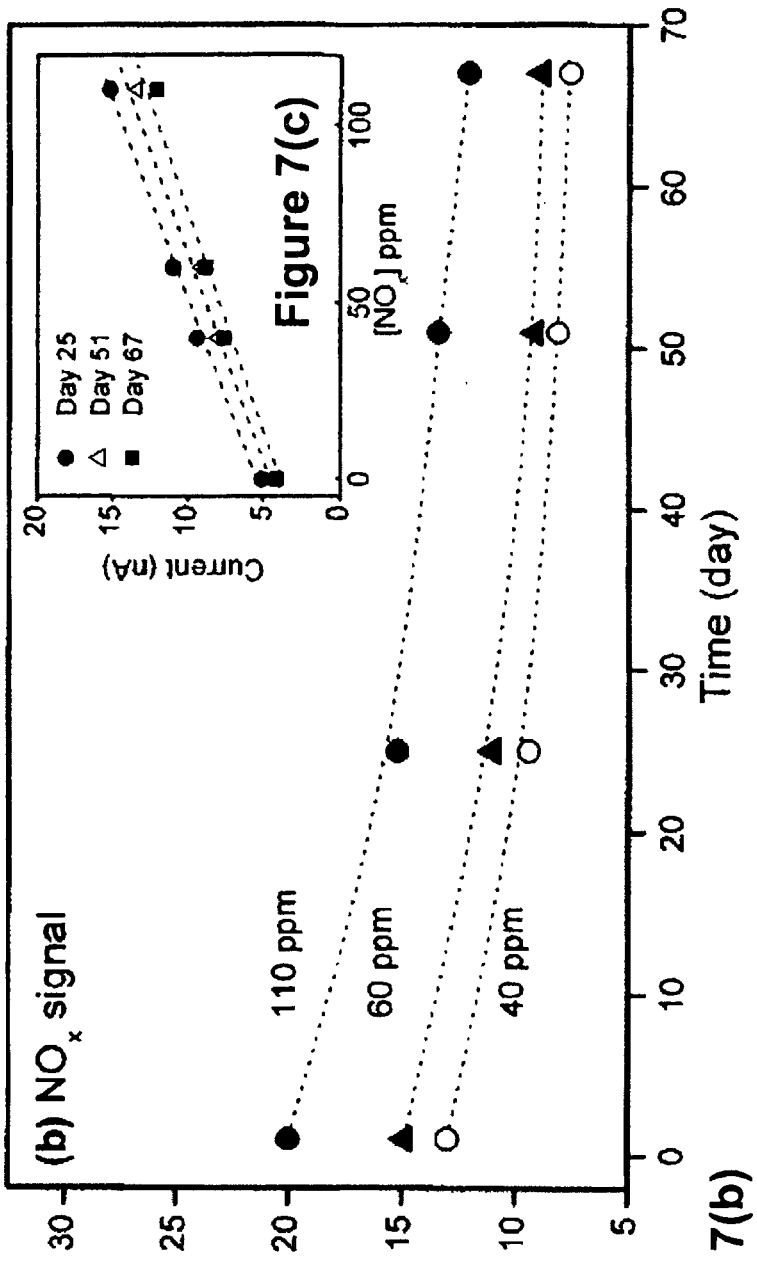

COMPACT ELECTROCHEMICAL BIFUNCTIONAL $NO_x/O_2$ SENSORS WITH INTERNAL REFERENCE FOR HIGH TEMPERATURE APPLICATIONS

CROSS REFERENCE TO RELATED PATENT APPLICATIONS

The present application claims priority to U.S. Provisional Patent Application No. 61/035,962 filed Mar. 12, 2008 incorporated herein by reference in its entirety.

STATEMENT OF GOVERNMENT INTEREST

The United States Government has certain rights in this invention pursuant to Contract No. W-31-109-Eng-38 between the United States Government and the University of Chicago and/or pursuant to Contract Nos. DE-ACO2-06CH11357 and DE-PS26-02NT41422 between the United States Government and UChicago Argonne, LLC representing Argonne National Laboratory and grant DE-FC 26 03NT41615 to Ohio State University.

FIELD OF THE INVENTION

This invention is directed generally to an electrochemical sensor. More particularly, the invention is directed to a system and a method for use of electrochemical bifunctional $NO_x/O_2$ sensors. This sensor system employs a combination of two different electrochemical $NO_x$ measuring techniques, amperometric and potentiometric, to sense both $O_2$ and total $NO_x(NO+NO_2)$.

BACKGROUND OF THE INVENTION

Industrial systems as well as automotive and truck applications require monitoring of various gas compositions, such as $O_2$, $NO_x$, CO and $CO_2$, in a combustion environment to insure efficient, non-polluting operations. For instance, carefully controlling the oxygen level in boilers can maximize energy output and minimize pollutant emissions. It is estimated that yearly savings of $409 million from coal-fired power plants could be enabled through combustion optimization. In view of increasing commercial demands and legal requirements for decrease of pollutants, such sensor systems are extremely important. For example $NO_x(NO+NO_2)$ sensing is considered as one of the key elements of next generation internal combustion engines; and thus accurate and reliable $NO_x$ sensors must be developed to monitor $NO_x$ breakthrough to activate regeneration of $NO_x$ absorption catalysts and/or to control the injection of reductants for continuous $NO_x$ reduction. Further, for automotive and truck applications, the monitoring and control of both $NO_x$ and $O_2$ is necessary for emission control and/or air-to-fuel ratio measurement to maximize efficiency and reduce pollutants.

Conventional oxygen sensors require a continuous source of reference air to measure accurately the content of oxygen in the combustion of gases. This requirement increases the complexity and cost of oxygen sensing systems. Most high temperature sensors capable of detecting $O_2$ and $NO_x$ are based on stabilized zirconia, which has high ionic conductivity, as well as good mechanical and chemical stability at high temperatures. Zirconia oxygen sensors have long been used to monitor the performance of internal combustion engines in automobiles in order to increase the fuel efficiency and minimize emissions. The use of an external oxygen reference is the most common approach to detect oxygen. In this design, air is provided from outside the combustion environment to a reference electrode that is separated from the sensing environment by a zirconia channel. The oxygen concentration differential between the outside and the measuring environment generates an open circuit potential that obeys the Nernst law, allowing for direct calculation of the unknown concentration of oxygen. For $NO_x$ detection, a multistage configuration in which gases in the combustion environment diffuse through a narrow channel into one or two chambers constructed of laminated YSZ (yttria-stabilized zirconia) sheets. The first chamber is normally equipped with oxygen pumping electrodes, which can selectively remove oxygen from the gas mixture to minimize the oxygen interference. A pair of noble metal electrodes then electrochemically converts the $NO_x$ mixture into NO or $NO_2$ exclusively, which is detected by either potentiometric or amperometric methods at the last stage.

Nevertheless, although great effort has been devoted to develop $NO_x/O_2$ dual sensors with the multi-stage configuration, a commercially successful product has still not been achieved. In order to construct gas chambers and introduce reference air from the external environment, a number of YSZ sheets and insulation layers (up to about thirteen separate layers) need to be well aligned and laminated. This process drastically increases the complexity of sensor fabrication and compromises the sensor durability under thermal shock and thermal cycles. On the other hand, it is beneficial to use more than one gas sensor in more than one location to optimize performance in multi-cylinder engines. A sensor that requires external air constrains the location of sensors inside the combustion environment and impedes the development toward sensor miniaturization. Consequently, a system meeting all the increasing needs of industrial applications has yet to be achieved.

SUMMARY OF THE INVENTION

In order to achieve a dual $O_2$ and $NO_x$ sensor that requires no external reference gas and is cost effective, two electrochemical, total $NO_x$ measuring techniques are coupled with a metal/metal oxide internal oxygen reference to sense both $O_2$ and $NO_x$ simultaneously using a single sensor within a given combustion environment. For example, a metal oxide (such as Pd/PdO) containing reference chamber was sealed within a stabilized zirconia superstructure by a high pressure/temperature bonding method that initiated grain boundary sliding between the ceramic components to enable proper bonding. Amperometric and potentiometric $NO_x$ sensing devices were disposed on an external portion of the Pd/PdO chamber. Pt-loaded zeolite Y was used to obtain total $NO_x$ capacity and to cover the Pt electrodes used for detecting the oxygen component in the presence of $NO_x$. Both of the amperometric and potentiometric sensors achieved good $NO_x/O_2$ signal stability, total $NO_x$ response and virtually insignificant $NO_x$—$O_2$ cross interference. Since there is no need for reference gas components, the sensors can be more readily and efficiently positioned in a gas combustion environment.

These and other objects, advantages and features of the invention, together with the organization and manner of operation thereof, will become apparent from the following detailed description when taken in conjunction with the accompanying drawings.

BRIEF DESCRIPTION OF THE DRAWINGS

FIG. 5A illustrates EMF versus log $[NO_x]$ plots for a potentiometric configuration at 600° C. with gases passing through a PtY filter (at 400° C.) with $O_2$ at 3%; FIG. 5B illustrates EMF transient responses for 1, 5, 10 and 13.5 ppm $NO_2$ in the presence of 3% $O_2$; and FIG. 5C illustrates response transients for NO in the presence of 3% $O_2$;

FIG. 6A illustrates amperometric $NO_x$ current signals over time at 500° C. and 100 ppm $NO_2$ for corresponding different $O_2$ signal levels of FIG. 6B; and FIG. 6C illustrates potentiometric $NO_x$ EMF signals over time at 600° C., with a PtY filter at 400° C. and 100 ppm $NO_2$ for corresponding different $O_2$ signal levels of FIG. 6D;

FIG. 7A illustrates EMF output for an oxygen signal on amperometric configuration at 500° C. over a sixty-seven day testing period (abscissa shown in FIG. 7B) for two levels of $O_2$ percentage; FIG. 7B illustrates current output for the amperometric configuration for different levels of $NO_2$; and FIG. 7C shows current versus $[NO_x]$ plots versus current for different time periods of measurements.

DETAILED DESCRIPTION OF VARIOUS EMBODIMENTS

Figures 1A, 1B, 1C:
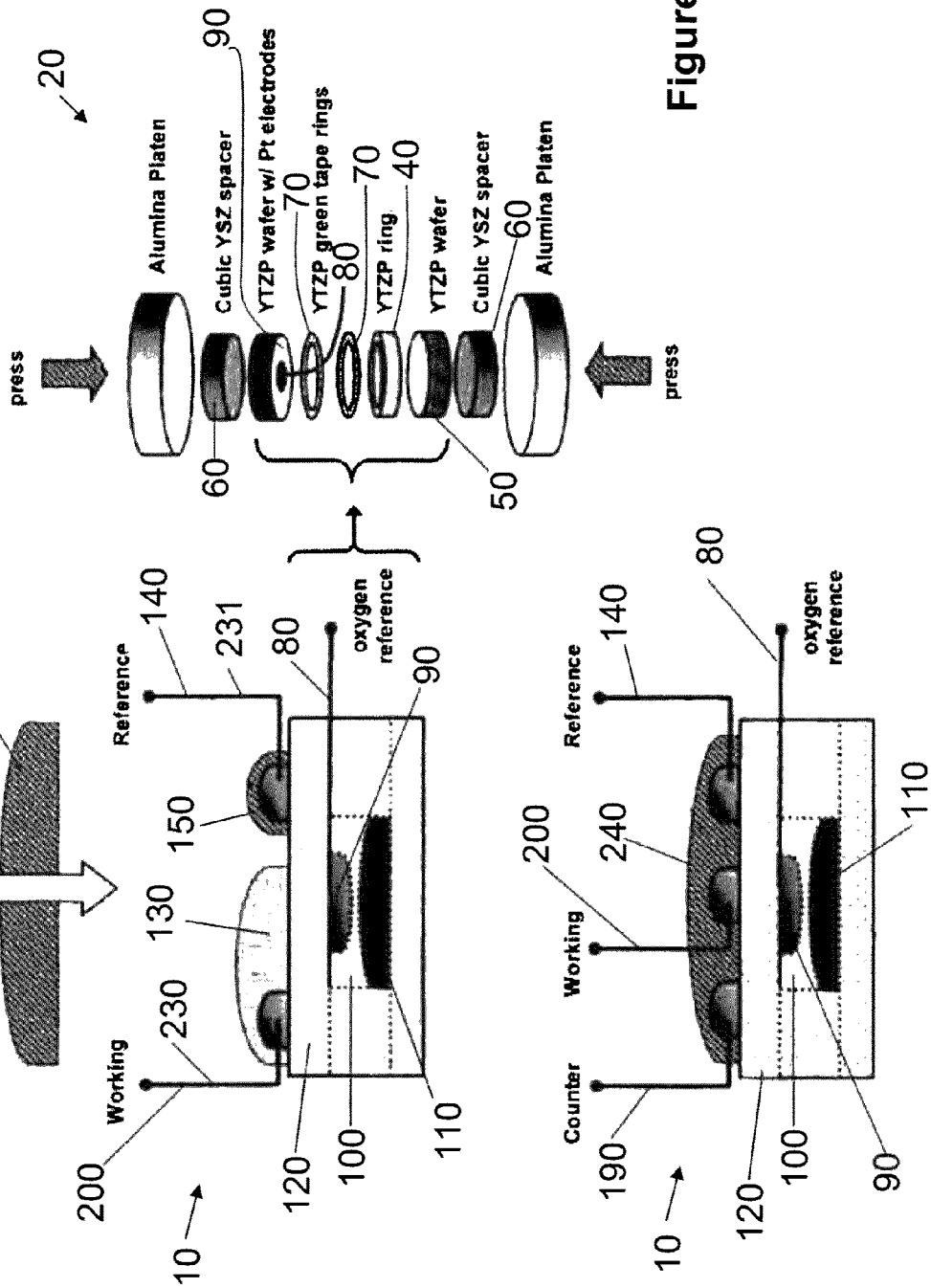
FIG. 1A illustrates a cross-sectional view of a sensor assembly in a potentiometric configuration and a separate Pt-zeolite filter (PtY)
FIG. 1B illustrates an amperometric configuration operating of the sensor.
FIG. 1C is an exploded view of the components of a Pd/PdO chamber assembly wherein cubic YSZ spacers and alumina platens are removed upon joining (not part of final operating assembly)

A bifunctional sensor assembly 10 constructed in accordance with concepts of the invention is shown in FIGS. 1A-1C. A basic package superstructure 20 is constructed in an embodiment as shown in FIG. 1C using a plurality of components. A YTZP ring 40 and a bottom wafer 50 were preferably cut from densified rods/tubes of 3 mol % yttria-stabilized tetragonal zirconia polycrystals (YTZP, Custom Technical Ceramics). The 8 mol % cubic yttria-stabilized zirconia spacers 60 were cut from a rod (supplied by Custom Technical Ceramics). The YTZP green tapes 70 (Nextech Materials) were laser cut from sheets into rings that matched the YTZP rings 40 cut from tubes. The Pt wire 80 (99.95%, 0.13 mm in diameter, Fischer Scientific) to the inner reference electrode 90 was sandwiched between the two pieces of YTZP green tape 70. The assembly 10 was then constructed by sealing PdO (Alfa Aesar) into a reference chamber 100. A mixture of Pd/PdO 110 is formed at the sensor operating temperature along with the reference $P(O_2)$ as predicted by the Ellingham diagram. In other embodiments, other transition metals and oxides of the transition metal may also be used, for example, Ni/NiO, Co/CoO, Fe/$Fe_2O_3$, Rh/$Rh_2O_3$, among others. A small amount of 8 mol % YSZ powder (TZ-8Y, Tosoh) was placed on top of PdO 110 to prevent alloying with the Pt wire 80 of the reference electrode 90. The Pt loaded zeolite Y powder was prepared and characterized as explained in Example I. Each "sandwich" superstructure 20 as shown in FIG. 1C was processed as explained in Example II.

As shown in FIG. 1A the potentiometric arrangement was prepared by first finishing the assembly 10, and then two Pt lead wires 230/231 were attached to the top of the assembly 10 with a small amount of commercial Pt ink (Englehard, A4731). The end of the Pt lead wire 230 that is attached to the YSZ 120 was shaped into a disc of 2 mm diameter in order to increase the mechanical stability. The Pt ink was cured at 1200° C. for two hours to secure bonding between the Pt wire 230 and the YSZ 120. $WO_3$ powder was mixed with α-terpineol to form a paste, which was then painted on top of the Pt lead wire 230 and the YSZ 120. A resulting $WO_3$ layer 130 was spread over as much of the YSZ 120 as possible. In other embodiments, other transition metal oxides and mixed transition metal oxides may be used as sensing electrodes. For example, a mixed transition metal oxide comprising lanthanum strontium iron cobalt oxides may be used in various embodiments. After sintering at 700° C. in air for 2 hours, the $WO_3$ layer 130 was typically about 200 μm thick. PtY was also mixed with α-terpineol and painted on top of another Pt lead wire 231 to form a reference electrode 140. The PtY layer 150 is around 100 μm thick after calcination in air at 600° C. for about two hours.

In the amperometric arrangement instead of two Pt lead wires being placed on top of the sensor assembly 10 for the potentiometric sensor, three Pt wires (working 200, counter 190 and reference 140) were mounted on the amperometric form of the sensor 10 (see FIG. 1B). At 500° C., the Pt reference electrode 140 on the YSZ 120 cannot be a good reversible electrode. A counter electrode 190 is therefore required for accurate potential control. The reference electrode 140 was kept well separated from working electrode 200 and the counter electrode 190 to reduce electrical interference. The PtY 240 was mixed with α-terpineol to form a paste and then painted on top of all three of the electrodes 140, 190, and 200. The sensor assembly 10 was heated in 650° C. air for 2 hours and then cooled back to 500° C. for sensing analyses.

Figure 3:
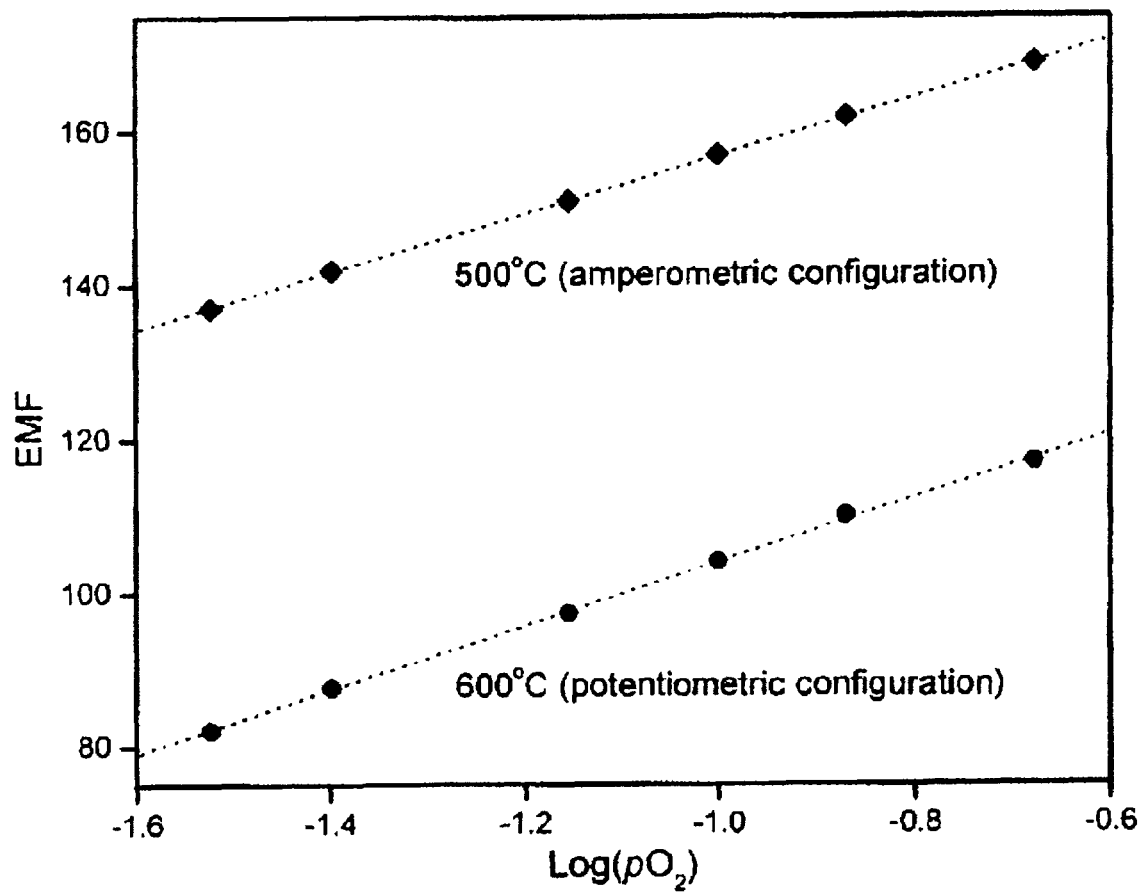
FIG. 3 illustrates the oxygen sensing behavior of both the amperometric and potentiometric configurations as EMF versus log $[P(O_2)]$ plots at 500° C. (amperometric configuration) and 600° C. (potentiometric configuration)

The oxygen sensing behavior was first examined at 500° C. and 600° C., the most preferred working temperatures for the amperometric and potentiometric $NO_x$ sensing configurations. As shown in FIG. 3, the open circuit potential between the Pd/PdO internal reference electrode 90 and the PtY reference electrode 140, exhibits Nernstian behavior at both temperatures. At 600° C., the calculated internal $P(O_2)$ is lower than the theoretical $P(O_2)$ created by Pd/PdO. One of the possible reasons for the deviation is that the temperature experienced by the sensor is slightly different from the furnace setting. For example, the sensor assembly 10 might not be located at the center of the heating zone, and a 5-1° C. temperature deviation could be measured.

Figure 4A:
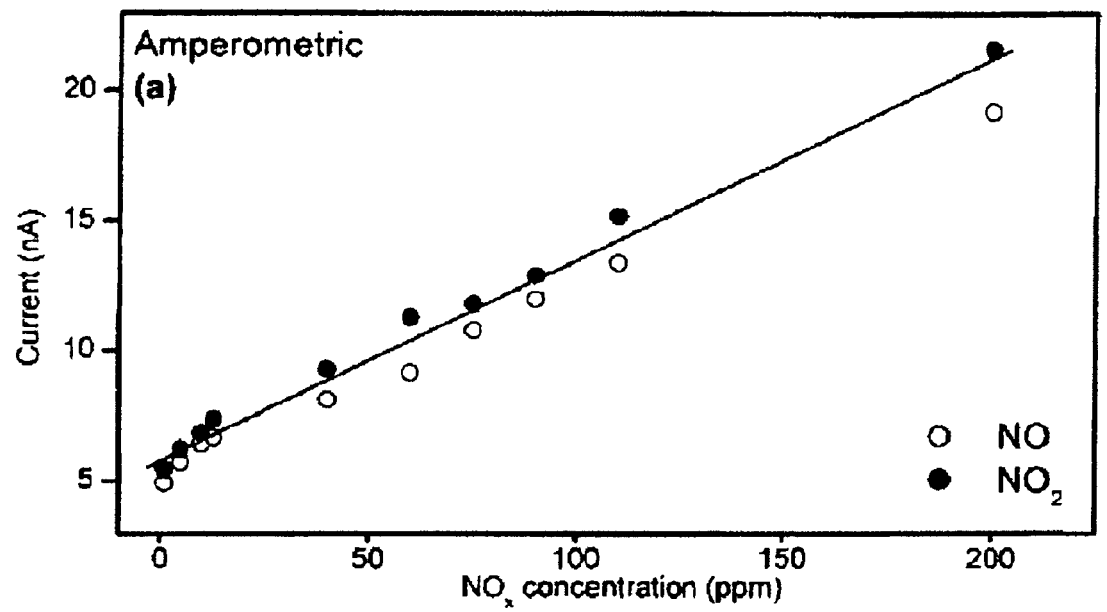
FIG. 4A illustrates current versus $[NO_x]$ plots for an amperometric configuration at 500° C. in 3% $O_2$.
Figures 4B, 4C:
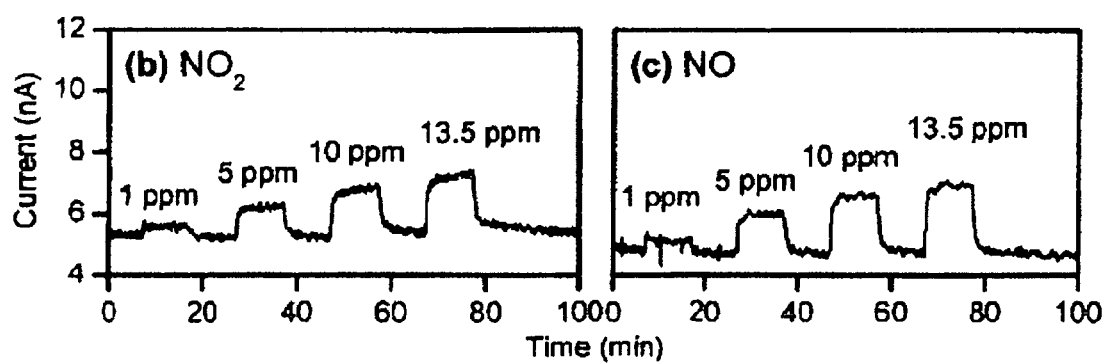
FIG. 4B illustrates transient current response versus time for 1, 5, 10 and 13.5 ppm $NO_2$ in 3% $O_2$.
FIG. 4C illustrates transient current response versus time for NO in 3% $O_2$.

In FIG. 4A the NO and $NO_2$ concentration was changed from 1 ppm to 200 ppm to check the $NO_x$ sensing performance of the amperometric sensor. The amperometric form of the sensor 10 (FIG. 1B) at 500° C. was anodically polarized to 80 mV (versus the PtY reference electrode 140); and the current in the presence of 1-200 ppm $NO_x$ in 3% $O_2$ was recorded with gases passing through the PtY overcoat 240. The bias potential of 80 mV was chosen based on the I-V behavior since a measurable current in the presence of $NO_x$ was expected. The calibration plot in FIG. 4A exhibits a linear relationship between current and the concentration of $NO_x$. The similarity of response transients in FIGS. 4B and 4C to NO and $NO_2$ in the concentration range of 1-13.5 ppm demonstrates that the PtY thick film 150 coated on the sensor surface can equilibrate the $NO_x$ mixture; and the sensor assembly 10 produces a total $NO_x$ response.

A potentiometric form of the sensor assembly 10 was tested with the gas mixture passing through the PtY filter 220 heated at 400° C., which was chosen as the optimal filter temperature because maximum $NO_x$ signal was observed without the occurrence of catalytic reductions when $NH_3$ was also present. As shown in FIG. 5A, $NO_2$ and NO with the same concentration (5-600 ppm) generates almost the same potential on the sensor assembly 10; and the potential displays a logarithmic relation to $NO_x$ concentration. The use of the PtY filter 220 makes it possible to measure total $NO_x$ and reduce the interferences from CO, propane, $NH_3$ and $CO_2$. The intense $NO_x$ signal arises from dissimilarity of catalytic activity of PtY and $WO_3$. In other embodiments, other metal oxides and supported catalysts that are efficient for $NO_x$ equilibration may be used as the filter material. Catalytic activity measurements and temperature programmed desorption indicated that $WO_3$ was almost inactive toward $NO_x$ equilibration; and no chemisorbed $NO_x$ species was released from the $WO_3$ surface. On the contrary, PtY has much higher activity toward $NO_x$ equilibration. Therefore, on the $WO_3$ electrode 130, electrochemical reactions that generate the electric potential compete with weaker heterogeneous catalytic reactions (non-electrochemical reactions); and the opposite phenomenon happens on the PtY reference electrode 140.

Both types of the sensor assembly 10 (amperometric and potentiometric) were tested with 100 ppm $NO_2$ in oxygen levels from 4% to 13.5% to examine the cross interference between $NO_x$ and oxygen. In FIGS. 6B and 6D, the oxygen signal does not have significant $NO_x$ interference from 100 ppm $NO_x$ since the covered PtY equilibrates $NO_x$ before it reached the triple-phase boundary. FIG. 6B was actually acquired after performing an "electrochemical pretreatment." Because of the low ionic conductivity of YSZ and high electrode interfacial impedance at 500° C., the sensor assembly 10 had sluggish $O_2$ response, which was not acceptable for real-time $O_2$ monitoring. In order to expedite the response, an electrochemical treatment was performed by polarizing the PtY reference electrode 140 to 500 mV for two hours, followed by relaxing the polarization in air overnight (also at 500° C.). This polarization treatment decreases the electrode interfacial impedance and the response time. This phenomenon remains effective for at last one week at 500° C. As shown in FIGS. 6B and 6D, the $O_2$ response time in 500° C. is almost the same as in 600° C. after the treatment. Electrochemical pretreatment has been applied to increase the stability and alter the impedance of electrodes in various electrochemical devices including glassy fiber detectors, sol-gel carbon composite electrodes, and zirconia sensors.

The oxygen interference with the $NO_x$ signal of the potentiometric device is not significant when the PtY filter 220 is applied (see FIG. 6C). For 100 ppm $NO_2$ only less than 10% relative error is observed when changing oxygen levels from 4% to 13.5%. The amperometric configuration has more pronounced oxygen interference with 39% relative error. Nevertheless, when a more accurate $NO_x$ reading is desired, the oxygen signal from the internal oxygen reference can be used to correct the $NO_x$ signal by performing calibration runs in advance. FIGS. 6A-6D indicate that both types of the sensor assembly 10 are capable of detecting $O_2$ and $NO_x$ simultaneously without substantial cross interference.

To examine the long-term stability of the sensor, an amperometric type sensor was tested at 500° C. for two months with $O_2$ (3%, 21%) and $NO_2$ (40-110 ppm), and the results are presented in FIGS. 7A and 7B. There is a drift in the $NO_x$ background signal with time, which approaches steady state after 1 month. The signal current vs. $[NO_x]$ curves obtained at various times have similar slopes (see FIG. 7C inserted), which implies that the signal drift could be corrected periodically from the baseline signal (0 ppm $NO_x$). For the oxygen signal, an extremely stable signal was measured during the two-month period with only 1% error.

Figure 8A:
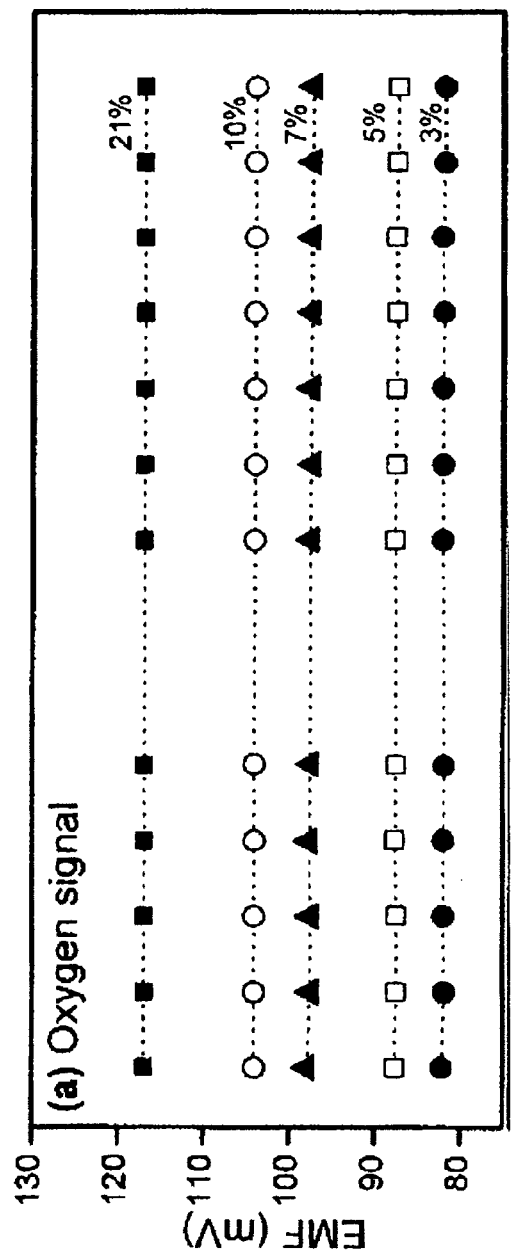
FIG. 8A illustrates the EMF output for an oxygen signal over time in a potentiometric configuration in 3%-21% $O_2$ without a PtY filter and FIG. 8B illustrates the EMF output for a $NO_x$ signal over time for 45 ppm-600 ppm $NO_2$ in 3% $O_2$.
Figure 8B:
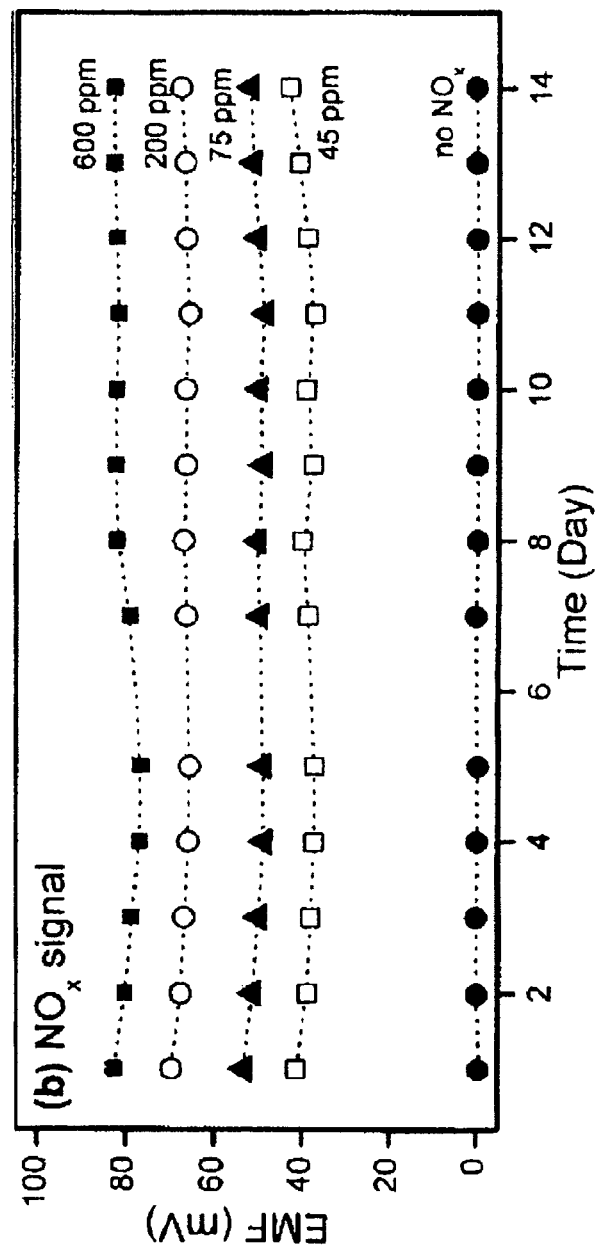

Signal change from a potentiometric sensor over a two-week period is shown in FIGS. 8A and 8B. Amounts of 45-600 ppm $NO_2$ and 3-21% $O_2$ were introduced to the test chamber each day without flowing through a PtY filter. Less than 0.5% error is observed from the oxygen signal. In the case of the $NO_x$ signal, the maximum error observed in the two-week period is 7.8%. The good stability of both types of sensor configurations indicates good thermal and chemical compatibility of sensor materials, including Pt, $WO_2$, PtY, YSZ, sealing glass, and PdO.

The difference of potentiometric and amperometric configurations are summarized in Table 1 below. Generally, the potentiometric sensor has more reliable signal and less oxygen cross interference. However, it required a separate filter housing and two sets of temperature controllers. The small size of the amperometric form of the sensor assembly 10 makes it attractive in certain applications. The drawbacks include the need of periodic calibration and the potential-control electronics is more costly, since the sensor is not operated in the limiting-current mode.

TABLE 1

Comparison of amperometric and potentiometric configurations.

| Configuration | Oxygen Response | $NO_x$ Response | $NO_x$ Interference to $O_2$ | $O_2$ Interference to $NO_x$ | Signal vs. $PO_2$ | Signal vs. $[NO_x]$ |
|---|---|---|---|---|---|---|
| Amperometric | Slow[a] | Fast | None | −39%[b] | Logarithmic | Linear |
| Potentiometric | Fast | Fast | None | −10%[b] | Logarithmic | Logarithmic |

| Configuration | Working Temperature | Size | Measurement | Temperature Control |
|---|---|---|---|---|
| Amperometric | 500° C. | very small (FIG. 1b) | voltmeter + potential control electronic (<$150) | one controller |

TABLE 1-continued

Comparison of amperometric and potentiometric configurations.

| Potentiometric | Sensor at 600° C. Filter at 400° C. | need filter housing | voltmeter | two controllers |

[a] can be improved by periodic electrochemical treatment
[b] can be minimized by using oxygen sensor data A Pd/PdO internal oxygen reference was coupled with two electrochemical total $NO_x$ measuring techniques to detect $O_2$ and $NO_x$ simultaneously in a combustion environment. A pressure and high temperature bonding method was used to create an effective physical seal of the Pd/PdO reference chamber, followed by building amperometric and potentiometric $NO_x$ sensing devices outside the chamber. PtY was used to obtain total $NO_x$ capacity and to cover the reference electrodes for detecting $O_2$ in the presence of $NO_x$. $WO_3$ was exploited with PtY to create dissimilarity of catalytic activity and generate intense potentiometric signal. Both amperometric and potentiometric types of the sensor assembly 10 show good $NO_x/O_2$ signal stability and total $NO_x$ response. Insignificant oxygen cross interference on $NO_x$ signal was observed. The good stability of both designs indicates good thermal and chemical compatibility of the materials of the sensors, including Pt, $WO_3$, PtY, YSZ, sealing glass, and PdO.

The following non-limiting examples illustrate various aspects of the invention.

Example I

The Pt-loaded zeolite Y powder was prepared and characterized as follows: Na-exchanged zeolite Y (Si/Al=2.5, Union Carbide, LZY-52) was prepared by ion-exchange. 1.0 g of NaY powder was dried at 100° C. for 4 hours followed by mixing with 2.5 mM $[Pt(NH_3)_4]Cl_2$ (Alfa Aesar) solution. The mixture was stirred overnight at room temperature for ion-exchange. After washing and centrifuging with distilled water several times, the Pt-exchanged powder was dried at 70° C. for 3 hours and then calcined at 300° C. for 2 hours. The heating rate of calcination was set to 0.2° C./min to increase the Pt dispersion by preventing autoreduction of the ammonia ligand. The calcined zeolite was exposed to 5% $H_2$ to reduce $Pt^{2+}$ in the zeolite framework to metallic Pt. The Pt content determined by ICP-OES in Galbraith Lab Inc. was 4.36%. $WO_3$ was used from a commercial powder (99.8%, Alfa Aesar) without any further treatment.

For material characterization, a FEI XL30 FEG ESEM was used to investigate the microstructure of PtY and $WO_3$. A Rigaku Geigerflex X-Ray Powder Diffractometer was applied to examine the crystal structure of PtY and $WO_3$. The dispersion of Pt clusters was inspected by FEI Tecnai TF-20 transmission electron microscope with the HAADF detector. The BET surface area was measured by Micrometrics ASAP 2020 analyzer.

Example II

The sandwich superstructure 20 of FIG. 1C was compressed in an argon atmosphere at temperatures ranging from 1250° C. to 1290° C. in a universal testing machine which is not shown (Instron, Model 1125) at crosshead speeds ranging from 0.01 mm/min to 0.02 mm/min. The strain rate used for all experiments was about $4\times10^{-5}s^{-1}$ in order to avoid overstressing the sample and damaging the Pt wire. In the >1250° C. temperature domain, this strain rate is expected to yield total stresses on a 1 $cm^2$ sample of less than 40 MPa. The system was allowed 30 minutes at the joining temperature to attain thermal equilibrium. Following joining, a glass (C153M glass, Asahi) was applied to the region of the sensor package where the Pt wire breached the inner-to-outer environment. C153M is a frit sealing glass composed of $SiO_2$, ZnO, and organic compounds (softens at 800° C., crystallizes at 910° C.). The glass powder was mixed with a-terpineol to make a slurry and a small amount was applied to the base of the Pt wire. The sensor was heated to 1200° C. for 3 hours to densify the glass plug.

Example III

Figure 2A:
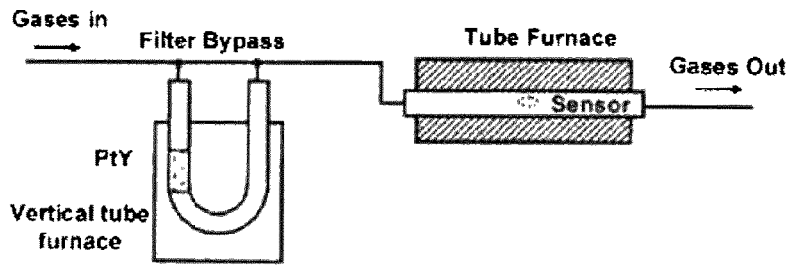
FIG. 2A illustrates a sensor assembly testing arrangement (PtY=Pt-zeolite Y)

The gas sensing experiments were performed by placing a quartz tube inside a tube furnace (Lindberg Blue, TF55035A). A computer-controlled gas delivery system with calibrated mass flow controllers (MFC) was used to introduce the test gases. Four certified $N_2$-balanced $NO_x$ cylinders (30 ppm NO, 30 ppm $NO_2$, 2000 ppm NO, and 2000 ppm $NO_2$ Praxair) were used as $NO_x$ sources. Sensor tests were carried out with mixtures of dry air, $NO_2$, and nitrogen with total gas flow rates of 200 cc/min at 500° C. or 600° C. As schematically shown in FIG. 2A, the gas mixture from MFCs could be introduced into the tube furnace either through or bypassing the PtY filter 220. The PtY filter 220 is a U-shape quartz tube with 100 mg PtY placed on quartz wool.

Figure 2B:
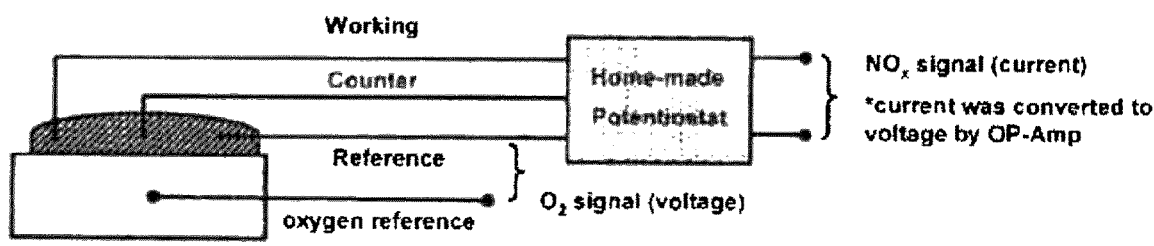
FIG. 2B illustrates a sensor measurement assembly for an amperometric configuration.
Figure 2C:
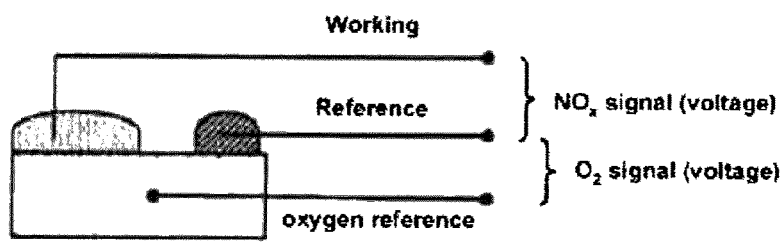
FIG. 2C illustrates a sensor measurement assembly for a potentiometric configuration.

Three (or four for the amperometric configuration) Pt wires were used to connect the sensor to external leads. For both configurations (FIGS. 2B and 2C), the open circuit potential between the oxygen reference and the PtY reference (the reference electrode 140 on the top of sensors, covered by PtY) was recorded by a multiplex data acquisition system (HP 34970A) with 10 GΩ internal impedance. The oxygen reference electrode 140 was connected to the negative terminal of the HP multimeter. For the amperometric configuration (FIG. 2B), a homemade portable potentiostat was used to apply a constant potential on the working electrode 200. The current (nA range) was converted to voltage (mA range) by a RCA 3140 OP-Amp and was measured also by the HP multimeter. In the potentiometric configuration (see FIG. 2C), the open circuit potential between the $WO_3$ layer 130 and PtY reference electrode 140 was measured by the HP multimeter with the PtY electrode 140 connected to the negative terminal.

The foregoing description of embodiments of the present invention have been presented for purposes of illustration and description. It is not intended to be exhaustive or to limit the present invention to the precise form disclosed, and modifications and variations are possible in light of the above teachings or may be acquired from practice of the present invention. The embodiments were chosen and described in order to explain the principles of the present invention and its practical application to enable one skilled in the art to utilize the present invention in various embodiments, and with various modifications, as are suited to the particular use contemplated.

What is claimed is:

1. A bi-functional sensor for sensing $NO_x$ and $O_2$ in a high temperature environment comprising:

a chamber comprising yttria-stabilized zirconia (YSZ) and forming an exterior surface and a substantially closed internal volume;
a first electrode disposed within the internal volume;
a quantity of a mixture of a first transition metal and an oxide of the first transition metal disposed within the internal volume;
a second electrode comprising a quantity of a second transition metal oxide disposed on the exterior surface of the chamber;
a third electrode comprising a quantity of Pt-zeolite Y disposed on the exterior surface of the chamber;
wherein the potential between the first electrode and the third electrode is indicative of the concentration of $O_2$ proximate the external surface, and wherein the potential between the second electrode and the third electrode is indicative of the $NO_x$ concentration proximate the external surface.

2. The bi-functional sensor of claim 1, further comprising a filter configured to be disposed between a combustion source and the bi-functional sensor, and wherein the filter comprises at least one of Pt-zeolite Y and a metal oxide with metal supported catalyst.

3. The bi-functional sensor of claim 1, wherein the first electrode comprises a first lead wire with a first end operatively connected to the YSZ and disposed within the internal volume and a second end extending from the external surface.

4. The bi-functional sensor of claim 1, wherein the chamber comprises yttria-stabilized tetragonal zirconia polycrystals (YTZP), and wherein the chamber includes a first substrate and a second substrate and a third substrate disposed between the first substrate and the second substrate and having a void configured to accept the quantity of the mixture of the first transition metal and the oxide of the first transition metal, and wherein the chamber is substantially sealed under a high temperature and a high pressure.

5. The bi-functional sensor of claim 1, wherein at least a portion of the bi-functional sensor is exposed to a combustion environment, and wherein the gas temperature of the combustion environment proximate the bi-functional sensor is between about 500° C. and about 600° C.

6. The bi-functional sensor of claim 1, wherein the first transition metal is selected from the group consisting of: Co, Fe, Ni, Pd and Rh.

7. The bi-functional sensor of claim 1, wherein the second transition metal oxide is selected from the group consisting of: cobalt oxide, NiO and $WO_3$.

8. The bi-functional sensor of claim 1, wherein the second transition metal oxide comprises a mixed transition metal oxide comprising a plurality of transition metals.

9. A bi-functional sensor for sensing $NO_x$ and $O_2$ in a high temperature environment comprising:
a chamber comprising yttria-stabilized zirconia (YSZ) and forming an exterior surface and a substantially closed internal volume;
a first electrode disposed within the internal volume and including a lead wire having a first end operatively connected to the YSZ, and a second end extending from the external surface;
a quantity of a mixture of a transition metal and an oxide of the transition metal disposed within the internal volume;
a quantity of Pt-zeolite Y disposed on the exterior surface of the chamber;
a second lead wire having a first end operatively connected to the quantity of Pt-zeolite Y and a second end operatively connected to a potential source; and
a third lead wire operatively connected to the quantity of Pt-zeolite Y,
wherein a current at the second and third electrodes is indicative of the concentration of $NO_x$ proximate the external surface, and wherein a potential between the first electrode and the third electrode is indicative of the concentration of $O_2$ proximate the external surface.

10. The bi-functional sensor of claim 9 further comprising a fourth lead wire operatively connected to the quantity of Pt-zeolite Y, and wherein the fourth lead wire comprises a counter electrode.

11. The bi-functional sensor of claim 9, wherein the quantity of Pt-zeolite Y is polarized to improve the response time for detection of the concentration of $O_2$.

12. The bi-functional sensor of claim 9, wherein the chamber comprises yttria-stabilized tetragonal zirconia polycrystals (YTZP), and wherein the chamber includes a first substrate and a second substrate, and a third substrate disposed between the first substrate and the second substrate and having a void configured to accept the quantity of the mixture of the first transition metal and the oxide of the first transition metal, and wherein the chamber is substantially sealed under a high temperature and a high pressure.

13. The bi-functional sensor of claim 10, further comprising a component electrically coupled to the second, third and fourth electrodes and configured to convert the current to a second voltage indicative of the concentration $NO_x$ proximate the sensor.

14. The bi-functional sensor of claim 6, wherein at least a portion of the bi-functional sensor is exposed to a combustion environment, and wherein the gas temperature of the combustion environment proximate the bi-functional sensor is between about 500° C. and about 600° C.

15. The bi-functional sensor of claim 9, wherein the transition metal is selected from the group consisting of: Co, Fe, Ni, Pd and Rh.

16. A method of simultaneously sensing a concentration of $NO_x$ and $O_2$ comprising:
providing a bi-functional sensor comprising a chamber forming a substantially closed internal volume and an external surface, a quantity of a reference material disposed within the internal volume, and a first electrode disposed within the internal volume, and a plurality of electrodes operatively coupled to the external surface of the chamber;
exposing the sensor to an atmosphere comprising a plurality of gases generated in a combustion environment;
obtaining a first electrical response from two or more of the plurality of electrodes indicative of the concentration of $NO_x$ in the combustion environment; and
obtaining a second electrical response from the first electrode and one or more of the plurality of electrodes indicative of the concentration of $O_2$ in the combustion environment.

17. The method of claim 16, wherein the chamber comprises a yttria-stabilized zirconia (YSZ), and wherein the quantity of the reference material comprises a mixture of a metal and an oxide of the metal.

18. The method of claim 16, wherein the bi-functional sensor comprises a potentiometric sensor configured such that the first electrical response comprises a first voltage indicative of the concentration of $NO_x$ in the combustion environment, and wherein the second electrical response comprises a second voltage indicative of the concentration of $O_2$ in the combustion environment.

19. The method of claim 18, wherein the chamber further includes a quantity of a first material disposed on the external surface and a quantity of a second material disposed on the external surface, and wherein the quantity of the first material and the quantity of the second material are electro-chemically responsive to the concentration of $NO_x$ in the combustion environment.

20. The method of claim 19, wherein the quantity of the first material comprises $WO_3$ and a first lead wire is coupled thereto, and wherein the quantity of the second material comprises Pt-zeolite Y and a second lead wire is coupled thereto.

* * * * *